(12) United States Patent
Fulton et al.

(45) Date of Patent: *Jul. 3, 2018

(10) Patent No.: US 10,010,380 B2

(54) BIOPSY LOCALIZATION METHOD AND DEVICE

(75) Inventors: Richard E. Fulton, Grand Junction, CO (US); William Richard Dubrul, Redwood City, CA (US)

(73) Assignee: Devicor Medical Products, Inc., Cincinnati, OH (US)

(*) Notice: Subject to any disclaimer, the term of this patent is extended or adjusted under 35 U.S.C. 154(b) by 2773 days.

This patent is subject to a terminal disclaimer.

(21) Appl. No.: 10/943,433

(22) Filed: Sep. 16, 2004

(65) Prior Publication Data

US 2005/0033195 A1    Feb. 10, 2005

Related U.S. Application Data

(63) Continuation of application No. 10/839,112, filed on May 4, 2004, now Pat. No. 8,292,822, which is a
(Continued)

(51) Int. Cl.
| | |
|---|---|
| *A61B 10/00* | (2006.01) |
| *A61B 90/00* | (2016.01) |
| *A61B 6/00* | (2006.01) |
| *A61B 10/02* | (2006.01) |
| *A61B 17/34* | (2006.01) |
| *A61B 17/00* | (2006.01) |

(52) U.S. Cl.
CPC ............. *A61B 90/39* (2016.02); *A61B 6/502* (2013.01); *A61B 10/02* (2013.01);
(Continued)

(58) Field of Classification Search
USPC ..... 600/431, 562, 492; 623/1.34, 1.15, 1.47, 623/11.11, 16.11, 1.1; 424/9.51, 9.52,
(Continued)

(56) References Cited

U.S. PATENT DOCUMENTS 2,899,362 A * 8/1959 Sieger, Jr. et al. ............ 604/368
3,001,522 A    9/1961 Silverman
(Continued)

FOREIGN PATENT DOCUMENTS

| DE | 935625 | 11/1955 |
|---|---|---|
| DE | 3913935 | 4/1989 |

(Continued)

OTHER PUBLICATIONS

Clarkson, P.: "Sponge Implants for Flat Breasts," Proceedings of the Royal Society of Medicine, vol. 53 at 880-881 (1960).
(Continued)

*Primary Examiner* — Michael C Stout
(74) *Attorney, Agent, or Firm* — Frost Brown Todd LLC

(57) ABSTRACT

Methods for localizing a biopsy site are disclosed. The method includes taking a tissue sample from a biopsy site and positioning a detectable, bioabsorbable element at the biopsy site at the time that the tissue sample was taken. The tissue sample is then tested. The biopsy site is then relocated by finding the bioabsorbable element. The bioabsorbable element may be made of collagen, gelatin, cellulose, polylactic acid, and/or polyglycolic acid. The detectable bioabsorbable element may be relocated using ultrasound or mammography. The bioabsorbable element may also swell upon contact with body fluid.

12 Claims, 3 Drawing Sheets

Related U.S. Application Data continuation of application No. 10/027,157, filed on Dec. 20, 2001, now Pat. No. 6,730,042, which is a continuation of application No. 09/900,801, filed on Jul. 6, 2001, now Pat. No. 6,699,205, which is a continuation of application No. 09/336,360, filed on Jun. 18, 1999, now Pat. No. 6,270,464.

(60) Provisional application No. 60/117,421, filed on Jan. 27, 1999, provisional application No. 60/114,863, filed on Jan. 6, 1999, provisional application No. 60/092,734, filed on Jul. 14, 1998, provisional application No. 60/090,243, filed on Jun. 22, 1998.

(52) U.S. Cl.
CPC ....... *A61B 17/3421* (2013.01); *A61B 17/3468* (2013.01); *A61B 2017/00004* (2013.01); *A61B 2090/3908* (2016.02); *A61B 2090/3962* (2016.02); *A61B 2090/3987* (2016.02)

(58) Field of Classification Search
USPC ........ 424/600, 422, 551; 606/198, 213, 151; 128/887; 604/103.1, 500
See application file for complete search history.

(56) References Cited

U.S. PATENT DOCUMENTS

| | | |
|---|---|---|
| 3,194,239 A | 7/1965 | Sullivan |
| 3,818,894 A | 6/1974 | Wichterle |
| 3,823,212 A | 7/1974 | Chvapil |
| 3,976,071 A | 8/1976 | Sadek |
| 3,996,938 A | 12/1976 | Clark, III |
| 4,007,732 A | 2/1977 | Kvavle |
| 4,034,759 A | 7/1977 | Haerr |
| 4,197,846 A | 4/1980 | Bucalo |
| 4,230,123 A | 10/1980 | Hawkins |
| 4,248,214 A | 2/1981 | Hannah |
| 4,298,998 A | 11/1981 | Naficy |
| 4,320,201 A | 3/1982 | Berg |
| 4,331,577 A | 5/1982 | Hanna |
| 4,356,572 A | 11/1982 | Guillemin |
| 4,425,908 A | 1/1984 | Simon |
| 4,438,253 A | 3/1984 | Casey et al. |
| 4,541,438 A | 9/1985 | Parker |
| 4,545,367 A | 10/1985 | Tucci |
| 4,592,356 A | 6/1986 | Gutierrez |
| 4,608,965 A | 9/1986 | Anspach, Jr. |
| 4,611,594 A | 9/1986 | Grayhack |
| 4,638,802 A | 1/1987 | Okada |
| 4,647,480 A | 3/1987 | Ahmed |
| 4,650,466 A | 3/1987 | Luther |
| 4,655,211 A | 4/1987 | Sakamoto et al. |
| 4,682,606 A | 7/1987 | Decaprio |
| 4,693,237 A | 9/1987 | Hoffmon |
| 4,744,364 A | 5/1988 | Kensey |
| 4,763,642 A | 8/1988 | Horowitz |
| 4,774,948 A | 10/1988 | Markham |
| 4,787,391 A | 11/1988 | Elefteriades |
| 4,789,401 A | 12/1988 | Ebinger |
| 4,799,495 A | 1/1989 | Hawkins |
| 4,813,422 A | 3/1989 | Fisher |
| 4,817,622 A | 4/1989 | Pennypacker |
| 4,832,686 A | 5/1989 | Anderson |
| 4,838,280 A | 6/1989 | Haaga |
| 4,847,049 A | 7/1989 | Yamamoto |
| 4,852,568 A | 8/1989 | Kensey |
| 4,907,589 A | 3/1990 | Cosman |
| 4,909,250 A | 3/1990 | Smith |
| 4,966,583 A | 10/1990 | Debbas |
| 4,970,298 A | 11/1990 | Silver |
| 4,986,279 A | 1/1991 | O'Neill |
| 5,002,548 A | 3/1991 | Campbell |
| 5,014,713 A | 5/1991 | Roper |
| 5,018,530 A | 5/1991 | Rank |
| 5,030,201 A | 7/1991 | Palestrant |
| 5,074,840 A | 12/1991 | Yoon |
| 5,080,655 A | 1/1992 | Haaga |
| 5,083,570 A | 1/1992 | Mosby |
| 5,085,629 A | 2/1992 | Goldberg |
| 5,100,423 A | 3/1992 | Fearnot |
| 5,102,415 A | 4/1992 | Guenther |
| 5,108,421 A | 4/1992 | Fowler |
| 5,120,802 A | 6/1992 | Mares |
| 5,127,916 A | 7/1992 | Spencer |
| RE34,056 E * | 9/1992 | Lindgren et al. ............ 600/567 |
| 5,148,813 A | 9/1992 | Bucalo |
| 5,158,084 A | 10/1992 | Ghiatas |
| 5,183,463 A | 2/1993 | Debbas |
| 5,183,464 A | 2/1993 | Dubrul |
| 5,186,922 A | 2/1993 | Shell et al. |
| 5,192,300 A | 3/1993 | Fowler |
| 5,195,540 A | 3/1993 | Shiber |
| 5,195,988 A | 3/1993 | Haaga |
| 5,197,482 A | 3/1993 | Rank |
| 5,204,382 A | 4/1993 | Wallace |
| 5,207,705 A | 5/1993 | Trudell |
| 5,221,269 A | 6/1993 | Miller |
| 5,236,410 A | 8/1993 | Granov |
| 5,281,408 A | 1/1994 | Unger |
| 5,282,781 A | 2/1994 | Liprie |
| 5,282,827 A | 2/1994 | Kensey et al. |
| 5,325,857 A | 7/1994 | Nabai |
| 5,326,350 A | 7/1994 | Li |
| 5,330,483 A | 7/1994 | Heaven |
| 5,334,216 A | 8/1994 | Vidal |
| 5,334,381 A | 8/1994 | Unger |
| 5,342,283 A | 8/1994 | Good |
| 5,353,804 A | 10/1994 | Kornberg |
| 5,388,588 A | 2/1995 | Nabai |
| 5,394,886 A | 3/1995 | Nabai |
| 5,409,004 A | 4/1995 | Sloan |
| RE34,936 E | 5/1995 | Campbell |
| 5,411,520 A * | 5/1995 | Nash et al. ................... 606/213 |
| 5,415,656 A | 5/1995 | Tihon |
| 5,417,697 A | 5/1995 | Wilk et al. |
| 5,422,730 A | 6/1995 | Barlow |
| 5,423,321 A | 6/1995 | Fontenot |
| 5,431,676 A | 7/1995 | Dubrul |
| 5,433,751 A | 7/1995 | Inoteb |
| 5,441,517 A | 8/1995 | Kensey et al. |
| 5,454,790 A | 10/1995 | Dubrul |
| 5,467,780 A | 11/1995 | Nabai |
| 5,469,854 A | 11/1995 | Unger |
| 5,479,936 A | 1/1996 | Nabai |
| 5,483,972 A | 1/1996 | Nabai |
| 5,487,392 A | 1/1996 | Haaga |
| 5,494,030 A | 2/1996 | Swartz |
| 5,507,813 A | 4/1996 | Dowd |
| 5,514,379 A | 5/1996 | Weissleder |
| 5,517,997 A | 5/1996 | Fontenot |
| 5,518,730 A | 5/1996 | Fuisz |
| 5,526,822 A | 6/1996 | Burbank |
| 5,549,560 A | 8/1996 | Von de Wijdeven |
| 5,556,410 A | 9/1996 | Mittermeir |
| 5,571,181 A | 11/1996 | Li |
| 5,571,182 A | 11/1996 | Ersek |
| 5,576,016 A | 11/1996 | Amselem |
| 5,591,204 A | 1/1997 | Janzen et al. |
| 5,626,611 A | 5/1997 | Liu |
| 5,634,883 A | 6/1997 | Chin |
| 5,636,255 A | 6/1997 | Ellis |
| 5,643,246 A | 7/1997 | Leeb |
| 5,643,282 A | 7/1997 | Kieturakis |
| 5,645,566 A | 7/1997 | Brenneman |
| 5,646,146 A | 7/1997 | Faarup |
| 5,647,374 A | 7/1997 | Crtrer |
| 5,656,297 A | 8/1997 | Bernstein |
| 5,660,185 A | 8/1997 | Shmulewitz |
| 5,670,161 A | 9/1997 | Healy |
| 5,676,146 A | 10/1997 | Scarborough |
| 5,676,925 A | 10/1997 | Klaveness |
| 5,688,490 A | 11/1997 | Tournier |
| 5,716,375 A | 2/1998 | Fowler |

(56) References Cited

U.S. PATENT DOCUMENTS

| | | |
|---|---|---|
| 5,716,404 A | 2/1998 | Vicante |
| 5,716,407 A | 2/1998 | Knapp |
| 5,735,289 A | 4/1998 | Pfeffer |
| 5,752,974 A | 5/1998 | Rhee |
| 5,792,157 A | 8/1998 | Mische |
| 5,794,626 A | 8/1998 | Kieturakis |
| 5,795,308 A | 8/1998 | Russin |
| 5,803,901 A | 9/1998 | Chin |
| 5,807,276 A | 9/1998 | Russin |
| 5,827,324 A | 10/1998 | Cassell |
| 5,868,708 A | 2/1999 | Hart |
| 5,869,080 A | 2/1999 | McGregor |
| 5,873,904 A | 2/1999 | Ragheb |
| 5,899,935 A | 5/1999 | Ding |
| 5,902,310 A | 5/1999 | Foerster |
| 5,922,024 A | 7/1999 | Janzen |
| 5,928,260 A | 7/1999 | Chin |
| 5,941,910 A | 8/1999 | Schindler |
| 5,980,564 A | 11/1999 | Stinson |
| 6,007,563 A | 12/1999 | Nash et al. |
| 6,015,541 A | 1/2000 | Greff |
| 6,027,520 A | 2/2000 | Tsugita |
| 6,053,876 A | 4/2000 | Fisher |
| 6,056,700 A | 5/2000 | Burney |
| 6,066,325 A | 5/2000 | Wallace |
| 6,071,301 A | 6/2000 | Cragg |
| 6,083,522 A | 7/2000 | Chu |
| 6,096,070 A | 8/2000 | Ragheb et al. |
| 6,113,629 A * | 9/2000 | Ken ............................. 623/1.1 |
| 6,136,014 A | 10/2000 | Sirimanne |
| 6,161,034 A | 12/2000 | Burbank |
| 6,162,192 A | 12/2000 | Cragg |
| 6,174,330 B1 | 1/2001 | Stinson |
| 6,183,497 B1 | 2/2001 | Sing |
| 6,214,045 B1 | 4/2001 | Corbitt |
| 6,228,055 B1 | 5/2001 | Foerster |
| 6,231,834 B1 | 5/2001 | Unger |
| 6,248,057 B1 | 6/2001 | Mavity |
| 6,261,241 B1 | 7/2001 | Burbank |
| 6,270,464 B1 | 8/2001 | Fulton |
| 6,271,278 B1 | 8/2001 | Park |
| 6,277,083 B1 | 8/2001 | Eggers |
| 6,309,420 B1 | 10/2001 | Preissman |
| 6,312,429 B1 | 11/2001 | Burbank |
| 6,331,166 B1 | 12/2001 | Burbank |
| 6,335,028 B1 | 1/2002 | Vogel |
| 6,340,367 B1 | 1/2002 | Stinson et al. |
| 6,347,241 B2 | 2/2002 | Burbank |
| 6,352,682 B2 | 3/2002 | Leavitt |
| 6,356,782 B1 | 3/2002 | Sirimanne et al. |
| 6,371,904 B1 | 4/2002 | Sirimanne |
| 6,376,742 B1 * | 4/2002 | Zdrahala et al. .......... 623/11.11 |
| 6,427,081 B1 | 7/2002 | Burbank |
| 6,589,502 B1 | 7/2003 | Coniglione |
| 6,605,047 B2 | 8/2003 | Zarins |
| 6,638,308 B2 | 10/2003 | Corbitt |
| 6,656,200 B2 | 12/2003 | Li et al. |
| 6,699,205 B2 | 3/2004 | Fulton |
| 6,730,042 B2 | 5/2004 | Fulton |
| 6,749,554 B1 | 6/2004 | Snow et al. |
| 6,774,278 B1 | 8/2004 | Ragheb et al. |
| 7,049,346 B1 | 5/2006 | Van Bladel et al. |
| 7,713,552 B2 * | 5/2010 | Bleyer et al. ................. 424/600 |
| 2001/0034528 A1 | 10/2001 | Foerster |
| 2002/0007130 A1 | 1/2002 | Burbank |
| 2002/0016555 A1 | 2/2002 | Ritchard |
| 2002/0019640 A1 | 2/2002 | McGuckin, Jr. |
| 2002/0026201 A1 | 2/2002 | Foerster |
| 2002/0026234 A1 | 2/2002 | Li |
| 2002/0035324 A1 | 3/2002 | Sirimanne |
| 2002/0107437 A1 | 8/2002 | Sirimanne |
| 2002/0193815 A1 | 12/2002 | Foerster |
| 2004/0049126 A1 | 3/2004 | Zarins |
| 2004/0049269 A1 | 3/2004 | Corbitt |
| 2004/0204660 A1 | 10/2004 | Fulton |
| 2004/0210160 A1 | 10/2004 | Fulton |
| 2004/0267155 A1 | 12/2004 | Fulton |
| 2005/0020916 A1 | 1/2005 | MacFarlane |

FOREIGN PATENT DOCUMENTS

| | | |
|---|---|---|
| DE | 4330958 | 3/1995 |
| DE | 4403789 | 8/1995 |
| EP | 146699 | 9/1987 |
| EP | 0255123 | 2/1988 |
| EP | 0350043 | 4/1990 |
| EP | 0481685 | 10/1991 |
| EP | 0534696 | 3/1993 |
| EP | 0769281 | 4/1997 |
| EP | 0293605 | 12/1998 |
| EP | 0894503 | 3/1999 |
| EP | 0966920 | 12/1999 |
| EP | 0983749 | 3/2000 |
| FR | 2714284 | 6/1995 |
| GB | 2020557 | 11/1979 |
| GB | 2132091 | 7/1984 |
| JP | 2001-510700 | 5/2001 |
| WO | WO 9015576 | 12/1990 |
| WO | WO 93/14712 | 5/1993 |
| WO | WO 9319803 | 10/1993 |
| WO | WO 9520370 | 1/1995 |
| WO | WO 96/08208 | 3/1996 |
| WO | WO 98/06346 | 2/1998 |
| WO | WO 98/10712 | 3/1998 |
| WO | WO 9847430 | 10/1998 |
| WO | WO 99/04704 | 2/1999 |
| WO | WO 0012009 | 3/2000 |
| WO | WO 0012010 | 3/2000 |
| WO | WO 00/38579 | 7/2000 |
| WO | WO 02/05717 | 1/2002 |
| WO | WO 02205717 | 1/2002 |

OTHER PUBLICATIONS

Dufrane, P. et al., "Prebiopsy Localization of Non-Palpable Breast Cancer," Journal Beige de Radiologies, vol. 73, No. 5, pp. 401-404 (Oct. 1, 1990).

Fournier et al: "Experimental Studies and Preliminary Clinical Trial of Vinorelbine-loaded Polymeric Bioresorbable Implants for the Local Treatment of Solid Tumors", Cancer Research 51, pp. 5384-5391, Oct. 1, 1991.

Ginde, Rajiv M., and Gupta, Rakesh K., "In Vitro Chemical Degradation of Poly (Glycolic Acid) Pellets and Fibers," Journal of Applied Polymer Science, vol. 33, pp. 2411-2429 (1987).

Hoffmann et al: "Biodegradable Implants in Orthopaedic Surgery—A Review on the State-of-the-Art,"; Clinical Materials; vol. 10, 1992; pp. 75-80.

Hoffmann: "Biodegradable Implants in Traumatology: Review on the State-of-the-Art,"; Arch Orthop Trauma Surg (1995) 114:123-132.

Pangman, W.J. and Wallace, R.M.: "The Use of Plastic Prosthesis in Breast Plastic and Other Soft Tissue Surgery," The Western Journal of Surgery, Obstetrics and Gynecology at 508 (Aug. 1955).

Hussman et al., "Optical Breast Lesion Localization Fiber: Preclinical Testing of a New Device," Radiology, 200:865-866 (Sep. 1996).

Hussman et al., "MR Mammographic Localization Work in Progress," Radiology, 189:915-917 (1993).

"Surgical Treatment of Breast Disease, Making the Diagnosis of Breast Cancer: Non-Palpable Breast Masses," BreastDoctor.com, http:/www.breastdoctor.com/breast/surgery/biopsy.htm.

"Surgical Treatment of Breast Disease: What's New? Diagnosing Breast Cancer: The ABBI Breast Biopsy System," BreastDoctor.com, http://breastdoctor.com/breast/surgery/abbi.htm.

* cited by examiner

BIOPSY LOCALIZATION METHOD AND DEVICE

This application is a continuation of U.S. application Ser. No. 10/839,112, filed May 4, 2004, which is a continuation of U.S. application Ser. No. 10/027,157, filed Dec. 20, 2001, now issued as U.S. Pat. No. 6,730,042, which is a continuation of U.S. application Ser. No. 09/900,801, filed Jul. 6, 2001, now issued as U.S. Pat. No. 6,699,205, which is a continuation of U.S. application Ser. No. 09/336,360, filed Jun. 18, 1999, now issued as U.S. Pat. No. 6,270,464, which application claims the benefit of the following Provisional patent applications: Biopsy Localization Device, Application No. 60/090,243, filed Jun. 22, 1998; Biopsy Localization and Hemostasis Device, Application No. 60/092,734, filed Jul. 14, 1998; Device and Method of Biopsy Localization and Hemostasis, Application No. 60/114,863, filed Jan. 6, 1999; and Device and Method of Biopsy Localization, Hemostasis & Cancer Therapy, Application No. 60/117,421, filed Jan. 27, 1999, all of the which are herein expressly incorporated by reference in the their entirety.

BACKGROUND OF THE INVENTION

In the U.S. alone approximately one million women will have breast biopsies because of irregular mammograms and palpable abnormalities. See FIG. 1 which diagrams the current treatment algorithm for non-palpable breast lesions. Biopsies can be done in a number of different ways for non-palpable lesions, including surgical excisional biopsies and stereotactic and ultrasound guided needle breast biopsies. In the case of image directed biopsy, the radiologist or other physician takes a small sample of the irregular tissue for laboratory analysis. If the biopsy proves to be malignant, additional surgery (typically a lumpectomy or a mastectomy) is required. The patient then returns to the radiologist a day or two later where the biopsy site (the site of the lesion) is relocated by method called needle localization, a preoperative localization in preparation for the surgery.

Locating the previously biopsied area after surgical excision type of biopsy is usually not a problem because of the deformity caused by the surgery. However, if the biopsy had been done with an image directed needle technique, as is common, help in relocating the biopsy site is usually needed. One procedure to permit the biopsy site to be relocated by the radiologist during preoperative localization is to leave some of the suspicious calcifications; this has its drawbacks.

Another way to help the radiologist relocate the biopsy site involves the use of a small metallic surgical clip, such as those made by Biopsys. The metallic clip can be deployed through the biopsy needle, and is left at the biopsy site at the time of the original biopsy. With the metallic clip as a guide, the radiologist typically inserts a barbed or hooked wire, such as the Hawkins, Kopans, Homer, Sadowski, and other needles, back into the patient's breast and positions the tip of the wire at the biopsy site using mammography to document the placement. The patient is then taken to the operating room with the needle apparatus sticking out of the patient's breast. While the clip provides a good indication of the biopsy site to the radiologist during preoperative localization, the clip remains permanently within the 80% of patients with benign diagnoses. Also, because the clip is necessarily attached to a single position at the periphery of the biopsy site, rather than the center of the biopsy site, its location may provide a misleading indication of the location of diseased tissue during any subsequent medical intervention. In addition, the soft nature of breast tissue permits the tip of the barbed or hooked needle to be relatively easily dislodged from the biopsy site. The clip is also relatively expensive.

Another localization method involves the use of laser light from the tip of a optical fiber connected to a laser. A pair of hooks at the tip of the optical fiber secures the tip at the biopsy site; the glow indicates the position of the tip through several centimeters of breast tissue. This procedure suffers from some of the same problems associated with the use of barbed or hooked wires. Another preoperative localization procedure injects medical-grade powdered carbon suspension from the lesion to the skin surface. This procedure also has certain problems, including the creation of discontinuities along the carbon trail.

SUMMARY OF THE INVENTION

The present invention is directed to a biopsy localization method and device which uses a locatable bioabsorbable element left at the biopsy site so that if testing of the biopsy sample indicates a need to do so, the biopsy site can be relocated by finding the bioabsorbable element. This eliminates the need to use of metallic clips during biopsies and often eliminates the need for a return to the radiologist for preoperative needle localization. In addition, the bioabsorbable element can be used as a therapeutic tool for treatment of the diseased lesion and for hemostasis.

A biopsy localization device made according to the invention includes a bioabsorbable element delivered in a pre-delivery state to a soft tissue biopsy site of a patient by an element delivery device. The bioabsorbable element may be palpably harder than the surrounding soft tissue at the biopsy site when in the post-delivery state.

One preferred material used as the bioabsorbable element is a dehydrated collagen plug. This type of plug may swell and is palpable for subsequent location by the surgeon. The collagen plug may not swell at all. In some situations, such as with small breasted women or where the biopsy site is close to the surface, a non-swellable bioabsorbable material, such as a round pellet of PGA, can be used instead of a swellable bioabsorbable material. The bioabsorbable material can also be made so that it is absorbed quickly to produce a local tissue inflammation; such a localized inflammation can be used to locate the biopsy site instead of location by palpation. Instead of leaving, for example, a collagen plug, a PGA pellet or a bioabsorbable suture material at the biopsy site for location by palpation or inflammation, a length of bioabsorbable suture material, a collagen filament, or other bioabsorbable material extending from the biopsy site out through the skin can be used. In this case the surgeon can follow the bioabsorbable suture material to the biopsy site in a manner similar to that used with Hawkins needles. In other cases, such as in the case of a deeply located lesion or large breast, the bioabsorbable material may need to be located by the radiologist, by for example, ultrasound or mammography. In any event the bioabsorbable material will typically be absorbed within about a month of placement. The invention thus eliminates the use of metal clips during biopsies and usually eliminates the need for return to the radiologist for preoperative localization.

While the primary use of the device is intended to localize the site of needle biopsies for possible future surgical excision, the device may also be useful in marking the site of surgical excisional biopsies. For example, during a wide surgical excision for cancer diagnosed by a recent surgical excisional biopsy, surgeons frequently have difficulty in determining the precise relationship of the previously excised tissue to the surgical wound. Therefore, more tissue is removed than might have been removed had the exact location of the previous lesion been more definite. With the present invention, a bioabsorbable element may be inserted into the biopsy site during a surgical excisional biopsy before the wound is closed to mark the site for potential wide excision should the biopsy reveal cancer. Alternatively, a bioabsorbable element may be placed at the biopsy site using a delivery device by partially or completely closing the wound and then depositing the bioabsorbable element through the delivery device and removing the delivery device through the closed incision. The presence of the palpable marker within the previous excisional biopsy site would allow the surgeon to more easily and confidently remove tissue around this site, and preserve more normal breast tissue.

Another use of the device is to primarily localize a non-palpable lesion prior to surgical excisional biopsy. Instead of using the needle/wire apparatus which has a tendency to migrate and become dislodged with traction, the palpable marker may be inserted into the suspicious area of the breast under mammographic or ultrasonic guidance immediately prior to the surgical excisional biopsy. This would provide a palpable locator for the surgeon as described above. In this instance, the marker would only need to be palpable, and not necessarily bioresorbable, since the intent would be to remove it in all cases.

In addition to permitting the biopsy site to be located by subsequent palpation or other means, the invention also can provide hemostasis and therapeutic benefits. The bioabsorbable element may comprise a therapeutic agent; the therapeutic agent may comprise at least a chosen one of a chemotherapeutic agent, a radiation agent and a gene therapy agent. Since the bioabsorbability can be varied from a day or two to a year or more, the material may be used to treat the diseased tissue and not just locate it. Some current therapies include radiation, chemotherapy, gene therapy as well as other technologies and therapies. Because the bioabsorbability can be easily varied, a medium can be place into the bioabsorbable element and be externally excited or triggered in those cases where the biopsy results are malignant. Further, the bioabsorbability concept can be used for future implantation of a therapeutic agent. For example, if the bioabsorbable element is a dehydrated collagen, this material could be used as a reservoir for, for example, delivery of materials that effect chemotherapy, brachytherapy, etc. Once the laboratory results are received and show the biopsy is malignant and therapy is required, by surgical excision or otherwise, the physician may inject, for example, a radiation pellet, a chemotherapeutic agent or a gene therapeutic agent into or adjacent to the bioabsorbable element for direct treatment of the diseased tissue.

The change in the bioabsorbable element can be via one of several ways, such as hydration or desiccation, change in temperature, electrical stimulation, magnetic stimulation, chemical or physical reaction with another material, additives, enzymatic reactions, ionization, electrical charges, absorption, as well as other means. The invention may employ one or more of these techniques or measures or others, to change the consistency, hardness and or size of the bioabsorbable element between its deployed and non-deployed states. The visual detectability of the bioabsorbable element may be aided by the use of a coloring agent, such as methylene blue or some other dye. The radiographic detectability of the element may be enhanced by a radiopaque marker. As well, ultrasonic detectability may be enhance by special treatment of the bioresorbable element.

The bioresorbable element may have margins which are roughened so as to prevent migration within the tissues. Filaments extending from the margins of the bioresorbable element may be utilized also to stabilize the position of the device within the cavity. The filaments may or may not be composed of the same material as the bioresorbable element.

The provision of hemostasis helps to lessen the bleeding and swelling within and about the biopsy site. This can be accomplished by physical or chemical means. That is, the device may swell so that it essential fills the biopsy cavity or the device may have a chemical reaction with blood or blood products to cause effective blood clotting, or both. Other methods for causing local hemostasis are also possible with the invention.

Other features and advantages of the invention will appear from the following description in which the preferred embodiments and methods have been set forth in detail in conjunction with the accompany drawings.

DESCRIPTION OF THE SPECIFIC EMBODIMENTS

Figure 1:
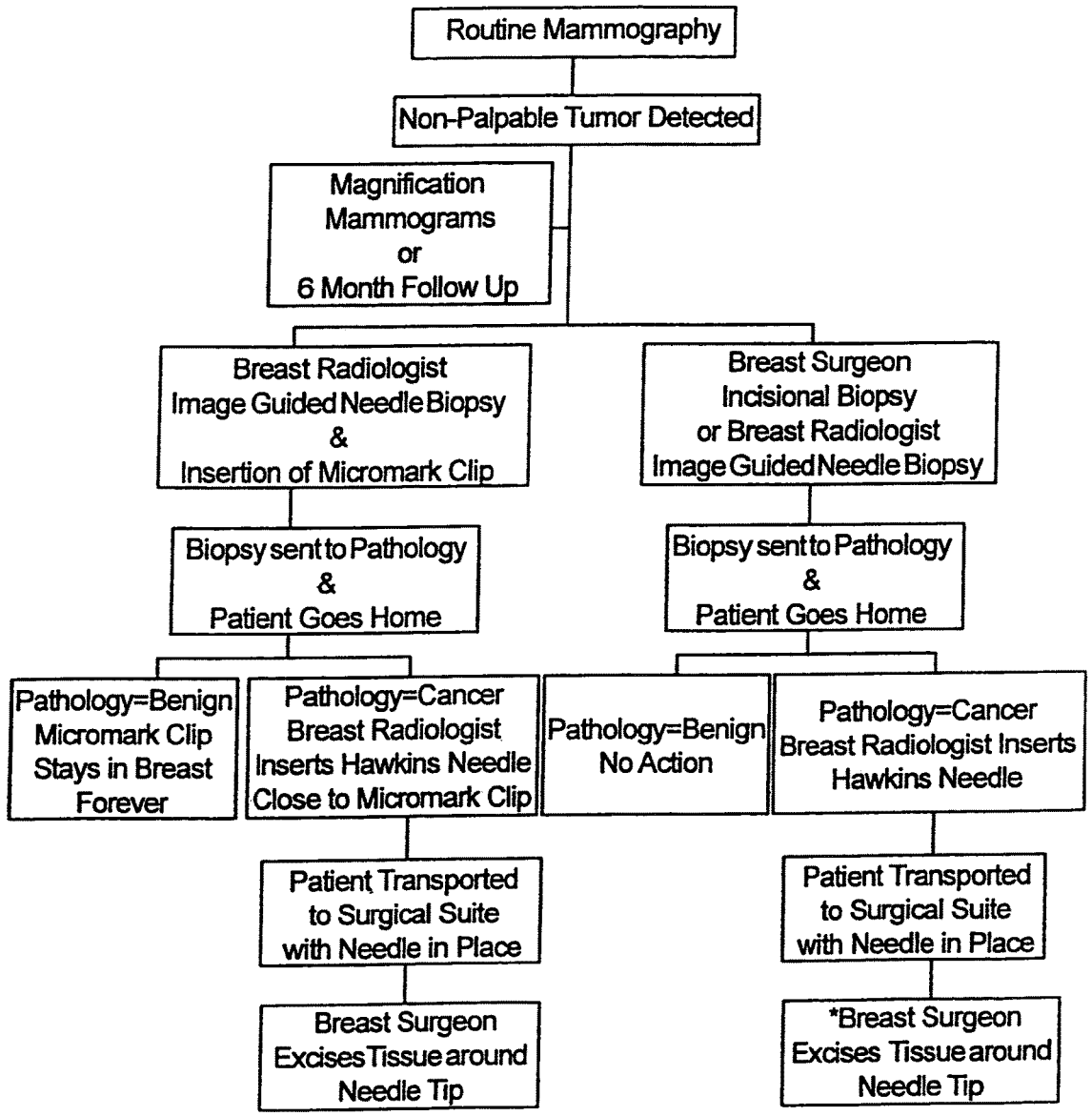
FIG. 1 is a flow diagram of a conventional treatment algorithm for nonpalpable breast lesions.
Figure 2:
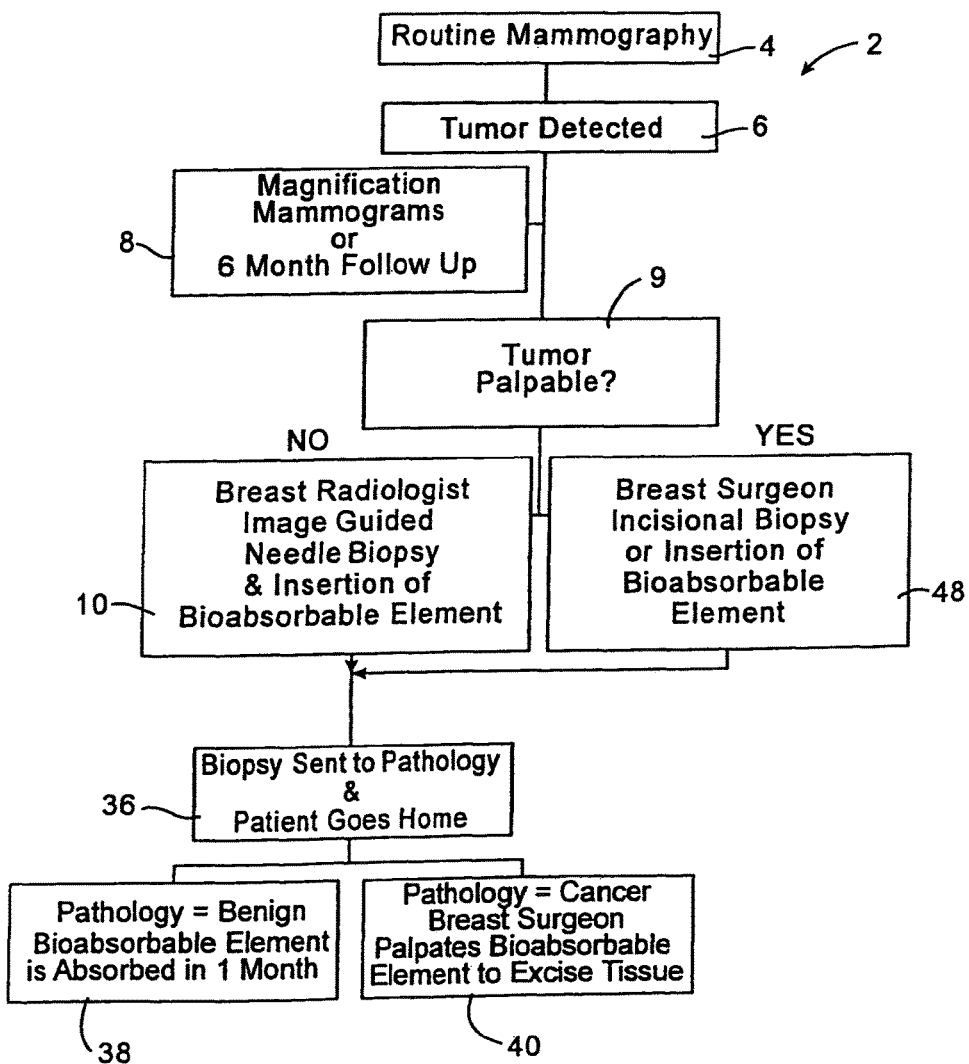
FIG. 2 is a flow diagram of a treatment algorithm according to the present invention.
Figure 3:
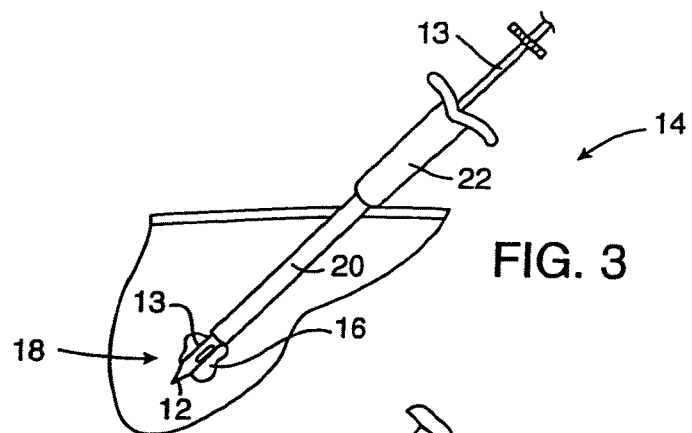
FIG. 3 is a simplified view illustrating a biopsy needle assembly obtaining a tissue sample of an abnormality at a target site.
Figure 4:
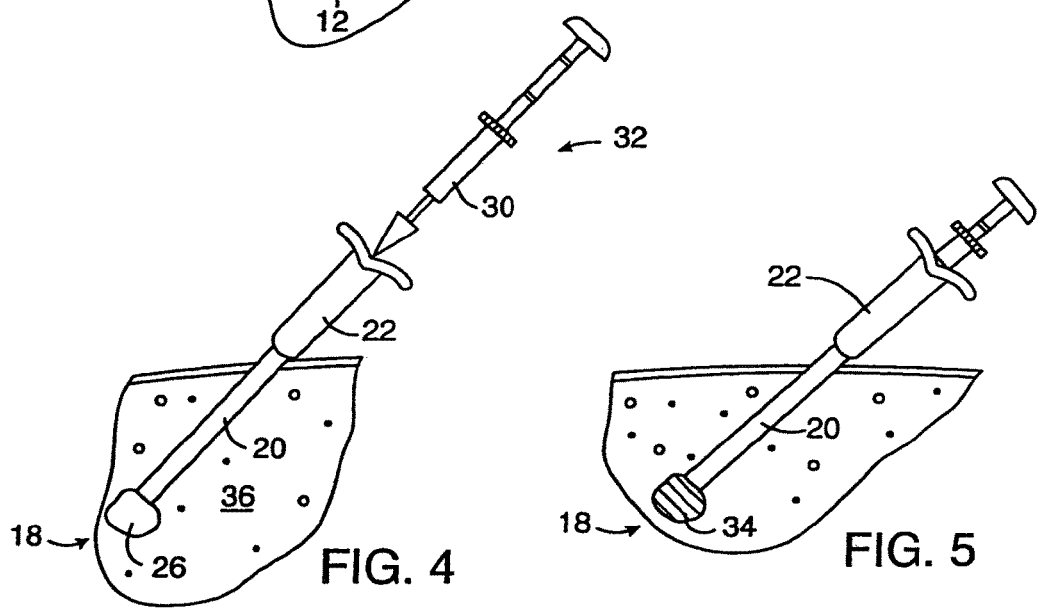
FIG. 4 illustrates the main housing and sheath of the needle biopsy assembly left in place after the tissue sample has been removed leaving a biopsied open region at the target site.
Figure 5:
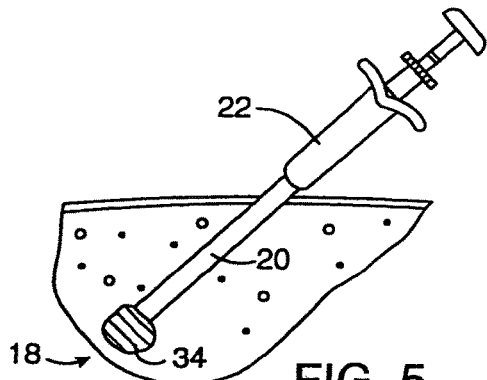
FIG. 5 illustrates the barrel of the delivery device of FIG. 4 inserted into the main housing of the biopsy needle assembly and the plunger depressed injecting the bioabsorbable element into the biopsied open region, thus effectively filling the biopsied open region at the target site.
Figure 6:
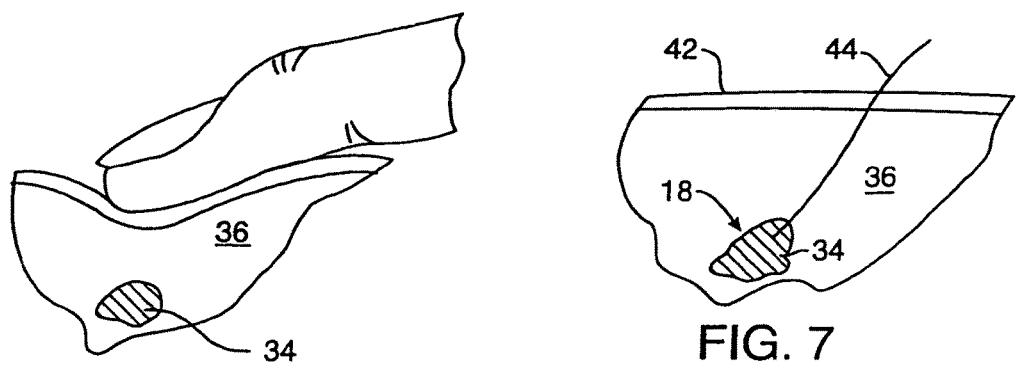
FIG. 6 illustrates the location of the bioabsorbable element of FIG. 5 with the surgeon using his or her fingers.

FIG. 2 illustrates a treatment algorithm 2 according to the present invention. As a result of a routine mammography 4, a tumor or other abnormality may be detected as at 6. The typical response will often include additional magnification mammograms or a follow-up mammogram scheduled for some time in the future, such as six months. This is indicated at 8. If the tumor is not palpable, see 9, an image guided needle biopsy by a breast radiologist is typically conducted as at 10. Image guided needle biopsies can be done in a number of ways. Presently, stereotactic (x-ray) and ultrasound guided needle biopsies are commonly used, primarily because of their accuracy, speed and minimal trauma to the patient. Stereotactic needle biopsies typically use a stereotactic table, such as made by Fisher or Lorad, which provides mammography (x-ray) guidance to a biopsy needle assembly. Ultrasound guided biopsies can be conducted with any one of a number of commercially available instruments. An exemplary biopsy needle assembly 14, illustrated in FIG. 3, includes a biopsy needle 13 passing through a sheath 20 extending from a hollow main housing 22. The tip 12 of biopsy needle 13 of biopsy needle assembly 14 is automatically inserted to the abnormality 16 at the target site 18. Biopsy needle 13 has a laterally directed side opening 24 adjacent to tip 12 used to capture a tissue sample of abnormality 16. Once the tissue samples have been obtained, the removed tissue creates a biopsied open region 26 at target site 18. See FIG. 4. Following the removal of biopsy needle 13 from sheath 20 and main housing 22, the barrel 30 of a bioabsorbable element delivery device 32 is inserted through main housing 22 and into sheath 20. Barrel 30 contains a bioabsorbable element 34, see FIG. 5 Bioabsorbable element 34 is, in this preferred embodiment, a plug of dehydrated collagen, such as that sold by several companies such as Davol, Datascope, Integra Life Sciences, Collagen Matrix, Vascular Solutions, et al. Bioabsorbable element 34 may swell on contact with an aqueous liquid within biopsied open region 26 and substantially fills the biopsied open region as suggested in FIG. 5. In this preferred embodiment, bioabsorbable element 34 is transformed from its pre-delivery state within barrel 30 to its post-delivery state at region 26 and in the process swells and becomes somewhat softer in its post-delivery state than in its pre-delivery state. However, in its post-delivery state, bioabsorbable element 34 is palpably harder, preferably at least about 1.5 times harder, than the surrounding soft tissue, typically breast tissue 36. This permits bioabsorbable element 34 at the target site 18 to be relocated by palpation of the patient by the physician, see FIG. 6, to find the bioabsorbable element 6 and as discussed in more detail below.

A bioabsorbable element could be made of materials other than collagen and could be in a form other than a solid, relatively hard plug in its pre-delivery state. For example, bioabsorbable element 34 in its pre-delivery state within barrel 30 could be in a liquid or otherwise flowable form; after being deposited at open region 26 at target site 18, the bioabsorbable element could change to become palpably harder than the surrounding tissue 36 to permit subsequent relocation of target site 18 by palpation. In some situations, it may be desired that bioabsorbable element 34 not change its size or hardness between its pre-delivery state and its post-delivery state, such as being palpably harder than the surrounding tissue 36 in both states. In a preferred embodiment, transformation of bioabsorbable element 34 is by contact with an aqueous liquid.

However, transformation of the bioabsorbable element, which can be in terms of, for example, hardness, texture, shape, size, or a combination thereof, can be due to other factors, such as application of thermal energy, radiation, magnetic energy, etc.

Returning again to FIG. 2, it is seen that after insertion of bioabsorbable element 34, the biopsy sample is sent to pathology for evaluation at 36. If the pathology report, which is available a day or two after the biopsy, is benign, the patient is so informed and the bioabsorbable element simply is absorbed by the patient within, for example, a month as at 38. If the pathology report is positive, so that cancer is found, the biopsied open region 26 at the target site 18 is located by the surgeon by palpation as suggested by FIG. 6. After finding the target site by palpation, which eliminates the need for preoperative localization by the radiologist, appropriate medical treatment, such as excisional surgery, can be performed.

If the tumor is palpable, the surgeon may choose to make a direct incisional biopsy as at 48. According to the present invention, bioabsorbable delivery device 32 could be used to place bioabsorbable element 34 at the site of the incisional biopsy. After removal of delivery device 32, the incision would be closed, the biopsy sample would be sent to pathology and the patient would go home with the procedure preceding as discussed above, starting with item 36.

It may be preferred that bioabsorbable element 34 also act as a hemostatic agent to stop bleeding at site 18 by virtue of physical means, by filling or substantially filling open region 26, as well as chemical means through the chemical interaction, such as coagulation, with blood components. In addition, bioabsorbable element 34 could be covered by a non-hemostatic degradable outer layer so that hemostasis or other action is delayed until the outer layer has been eroded. In some situations, it may be necessary or at least desirable to shield the bioabsorbable element from the blood or other body fluids until after the bioabsorbable element is in place at target site 18. This could be accomplished by, for example, physically isolating the bioabsorbable element from body fluids by using a removable physical barrier during delivery of the bioabsorbable element. Alternatively, a bioabsorbable coating or layer, as described above, may be used. The bioabsorbable element may be changed from its pre-delivery state to its post-delivery state in a variety of manners including hydration, changing the temperature, electrical stimulation, magnetic stimulation, chemical reaction with a stimulating agent, physically interaction with an activating member (such as a knife blade which could be used to slice open a capsule containing the bioabsorbable element), by ionizing the bioabsorbable element, or by absorption or adsorption of a fluid by the bioabsorbable element.

The invention may also be used to medically treat the patient. That is, the bioabsorbable element could include a therapeutic element which would be activated only if the pathology report indicated the need for the medical treatment. Various ways of activating an agent in a bioabsorbable element could be used, such as injecting a radiation-emitting element at the vicinity of the target site, externally irradiating the target site, providing a triggering substance to the target site, manual pressure, photodynamic therapy, sclerosing chemistry, vibrational therapy, ultrasound, and the like. Alternatively, the bioabsorbable element could be made so that it includes no such activating agent; rather, medical treatment could be provided by, for example, delivery of a chemotherapy agent, a radiation emitting element, thermal energy, electrical energy, vibrational energy, gene therapy, vector therapy, anti-angiogenesis therapy. To facilitate the delivery, the bioabsorbable element may contain a radiopaque marker or may have properties to aid in detecting it by ultrasound, in addition to being palpable.

An important use for the invention is in the treatment of breast cancer. In one embodiment, it is desirable that bioabsorbable element 34 in its post-delivery state have a hardness of at least about one and a half times that of breast tissue so that it is palpably harder than the surrounding tissue. Also, it is desired that bioabsorbable element 34, in one embodiment, swells from its pre-delivery state to its post-delivery state so to fill or at least substantially fills open region 26. To achieve this it is preferred that bioabsorbable element 34 swells about 50 to 1500%, and more preferably about 100 to 300%, from the pre-delivery state to the post delivery state, typically when placed in contact with an aqueous liquid. It is preferred that the bioabsorbable element has a longest dimension of at least about 0.5 cm in its post-delivery state to aid its location by palpation.

While the bioabsorbable element is preferably made of collagen in one embodiment, the bioabsorbable element can include, for example, one or more of the following materials; polyactic and polyglycolic acids, polyorthoesters, resorbable silicones and urethanes, lipids, polysaccharides, starches, ceramics, polyamino acids, proteins, hydrogels and other gels, gelatins, polymers, cellulose, elastin, and the like.

Figure 7:
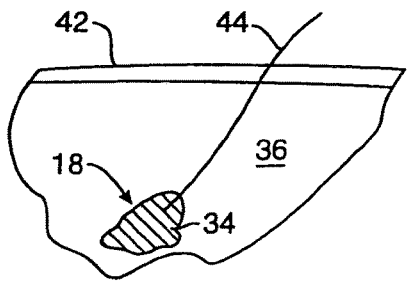
FIG. 7 illustrates a bioabsorbable thread extending from the bioabsorbable element of FIG. 5 up through the patient's skin, the thread being delivered to the bioabsorbable element using the delivery device of FIGS. 4 and 5.

In some situations it may be desired to use a bioabsorbable filament 44 extending from bioabsorbable element 34 through the patient's skin 46 as shown in FIG. 7. This can be accomplished by delivering bioabsorbable filament 44 through sheath 20 as bioabsorbable element 34 is injected into region 26 at target site 18. In some situations it may not be possible or desirable to use bioabsorbable element 34; in those situations it may be useful to provide for only bioabsorbable filament 44 extending from target site 18 to above the patient's skin 46.

While it is presently preferred that bioabsorbable element delivery device 32 be guided through a portion of needle assembly 14, that is sheath 20 and main housing 22, in some situations it may be useful to cover sheath 20 with an outer sheath which would be left in place after the biopsy sample has been removed and the entire biopsy needle assembly 14 has been removed. The sheath left in place would then be used to guide barrel 30 of delivery device 32 to target site 18. Of course, delivery device 32 could take a number of different forms such as a syringe containing fluid or paste that is injected through a needle or through the housing 22 and sheath 20 or through an outer sheath. Alternatively, other delivery devices could be employed for delivery of bioresorbable element 34.

The invention has applicability toward the correction of a defect that is caused by breast tissue removal for biopsy or diseased tissue removal. Collagen is often placed in the body where it is eventually replaced by human autogenous tissue. Hence, the invention could be used for the repair of tissue that has been damaged due to tissue removal. The delivery device described heretofore could be used for installing a material (synthetic or mammalian) into the cavity for such a cosmetic or reconstructive repair. The material would typically be an effectively non-bioabsorbable material, such as a silicon gel-filled capsule or bag.

Modification and variation can be made to the disclosed embodiments without departing from the subject of the invention as defined in the following claims.

Any and all patents, patent applications, and printed publications referred to above are incorporated by reference.

What is claimed is:

1. A biopsy method comprising:
   positioning a sheath and a biopsy needle with respect to a target site in tissue to be biopsied;
   extending the biopsy needle at least partially through the sheath;
   removing at least one tissue biopsy sample from the target site through the biopsy needle;
   removing the biopsy needle from the sheath while leaving the sheath positioned in the tissue at the target site;
   after the step of removing the biopsy needle, inserting a delivery device into the sheath, wherein the delivery device comprises at least one dehydrated bioabsorbable element including starch; and
   delivering the bioabsorbable element from the delivery device to the target site from which the tissue biopsy sample was removed.

2. The method of claim 1, further comprising relocating a biopsy site from which the tissue biopsy sample was removed by imaging the bioabsorbable element.

3. The method of claim 2, further comprising testing the tissue biopsy sample removed prior to the step of relocating the site.

4. The method of claim 1, wherein the bioabsorbable element has a pre-delivery state different from a post-delivery state.

5. The method of claim 1, wherein the bioabsorbable element has one consistency in the delivery device, and wherein the bioabsorbable element has a different consistency at a time after being delivered into the site from which tissue was removed.

6. A breast biopsy localization method comprising:
   positioning a sheath having a distal end with respect to a target site in breast tissue to be biopsied;
   taking a tissue sample from the target site within a patient by a needle biopsy device passing through and extending from the distal end of the sheath so as to create a biopsy site;
   removing the biopsy needle from the sheath while leaving the sheath in the breast tissue;
   without removing the sheath from the breast tissue, and after removing the biopsy needle from the sheath, inserting a bioabsorbable element delivery device into the sheath, wherein the bioabsorbable element delivery device contains at least one detectable bioabsorbable element;
   deploying the at least one detectable bioabsorbable element through the bioabsorbable element delivery device to mark the biopsy site from which the tissue sample was taken.

7. The method of claim 6, further including the step of relocating the biopsy site by imaging to find the detectable bioabsorbable element.

8. The method of claim 7, wherein the step of relocating the biopsy site by imaging comprises detecting the bioabsorbable element with ultrasound.

9. The method of claim 6, wherein the biopsy needle comprises a laterally directed side opening, and wherein the step of inserting the biopsy needle through and extending from the distal end of the sheath comprises positioning the laterally directed side opening beyond the distal end of the sheath.

10. The method of claim 6, wherein the detectable bioabsorbable element comprises a material selected from the group consisting of collagen, proteins, gelatins, starches, polysaccharides, ceramics, polyamino acids and hydrogels.

11. The method of claim 7, wherein the detectable bioabsorbable element has a pre-delivery state prior to its delivery to the target site, and a post-delivery state after being deployed to the target site, and wherein the post-delivery state is physically different from the pre-delivery state.

12. The method of claim 7, wherein the step of relocating the biopsy site comprises locating the detectable bioabsorbable element after the detectable bioabsorbable element swells from its pre-delivery state to its post-delivery state.

* * * * *